(12) United States Patent
Simons

(10) Patent No.: US 9,510,927 B2
(45) Date of Patent: Dec. 6, 2016

(54) METHOD OF MAKING A KNIT WITH BARBS

(71) Applicant: Sofradim Production, Trévoux (FR)

(72) Inventor: Damien Simons, Lyons (FR)

(73) Assignee: Sofradim Production, Trevoux (FR)

( * ) Notice: Subject to any disclaimer, the term of this patent is extended or adjusted under 35 U.S.C. 154(b) by 137 days.

(21) Appl. No.: 14/397,223

(22) PCT Filed: Jun. 27, 2013

(86) PCT No.: PCT/EP2013/063474
§ 371 (c)(1),
(2) Date: Oct. 27, 2014

(87) PCT Pub. No.: WO2014/001432
PCT Pub. Date: Mar. 1, 2014

(65) Prior Publication Data
US 2015/0315729 A1 Nov. 5, 2015

(30) Foreign Application Priority Data

Jun. 28, 2012 (FR) ...................................... 12 56168

(51) Int. Cl.
*A61F 2/00* (2006.01)
*D04B 21/14* (2006.01)
*D04B 21/12* (2006.01)

(52) U.S. Cl.
CPC ........... *A61F 2/0063* (2013.01); *A61F 2/0077* (2013.01); *D04B 21/12* (2013.01); *D04B 21/14* (2013.01);
(Continued)

(58) Field of Classification Search
CPC ...... A61F 2/0063; A61F 2/0077; D04B 21/12; D04B 21/14; D10B 2501/0632; D10B 2509/08
(Continued)

(56) References Cited

U.S. PATENT DOCUMENTS 3,054,406 A 9/1962 Usher
3,276,448 A 10/1966 Usher
(Continued)

FOREIGN PATENT DOCUMENTS

EP 1055757 A1 11/2000
EP 1158082 A2 11/2001
(Continued)

OTHER PUBLICATIONS

International Search Report for PCT/EP13/063474 date of completion is Nov. 21, 2013 (2 pages).

*Primary Examiner* — Leo B Tentoni

(57) ABSTRACT

The present invention relates to a method for producing a knit, said method comprising the following steps:—a) knitting first yarns of biocompatible polymer materials, a second yarn, which is a monofilament yarn, and a third yarn, which is a monofilament yarn, which are made of the same biocompatible hot-melt material, the diameter of the second yarn being strictly greater than the diameter of the third yarn:—said second and third yarns generating loops protruding from one face of said knit,—b) thermosetting the knit obtained at a),—c) placing the face of the knit with loops flat on a heated cylinder, resulting in i) the complete melting and elimination of the loops formed from the third yarn, and ii) the partial melting of the loops formed from the second yarn, said partial melting causing the rupture of each loop and, therefore, the formation, for each loop, of two barbs protruding outwards from the face of said knit.

15 Claims, 1 Drawing Sheet

(52) U.S. Cl.
CPC ... *D10B 2501/0632* (2013.01); *D10B 2509/08* (2013.01)

(58) Field of Classification Search
USPC .................. 264/103, 167, 234, 280; 66/195
See application file for complete search history.

(56) References Cited

U.S. PATENT DOCUMENTS

| | | | |
|---|---|---|---|
| 3,718,725 A | 2/1973 | Hamano | |
| 3,861,175 A * | 1/1975 | Farmer | D04B 21/02 66/210 |
| 3,887,699 A | 6/1975 | Yolles | |
| 4,767,628 A | 8/1988 | Hutchinson | |
| 4,931,546 A | 6/1990 | Tardy et al. | |
| 4,976,737 A | 12/1990 | Leake | |
| 5,106,629 A | 4/1992 | Cartmell et al. | |
| 5,116,357 A | 5/1992 | Eberbach | |
| 5,147,374 A | 9/1992 | Fernandez | |
| 5,195,542 A | 3/1993 | Gazielly et al. | |
| 5,201,745 A | 4/1993 | Tayot et al. | |
| 5,254,133 A | 10/1993 | Seid | |
| 5,258,000 A | 11/1993 | Gianturco | |
| 5,368,602 A | 11/1994 | de la Torre | |
| 5,370,650 A | 12/1994 | Tovey et al. | |
| 5,397,331 A | 3/1995 | Himpens et al. | |
| 5,593,441 A | 1/1997 | Lichtenstein et al. | |
| 5,634,931 A | 6/1997 | Kugel | |
| 5,676,967 A | 10/1997 | Williams et al. | |
| 5,695,525 A | 12/1997 | Mulhauser et al. | |
| 5,702,416 A | 12/1997 | Kieturakis et al. | |
| 5,711,960 A | 1/1998 | Shikinami | |
| 5,743,917 A | 4/1998 | Saxon | |
| 5,766,246 A | 6/1998 | Mulhauser et al. | |
| 5,769,864 A | 6/1998 | Kugel | |
| 5,916,225 A | 6/1999 | Kugel | |
| 5,919,232 A | 7/1999 | Chaffringeon et al. | |
| 5,922,026 A | 7/1999 | Chin | |
| 6,042,534 A | 3/2000 | Gellman et al. | |
| 6,090,116 A | 7/2000 | D'Aversa et al. | |
| 6,113,623 A | 9/2000 | Sgro | |
| 6,120,539 A | 9/2000 | Eldridge et al. | |
| 6,162,962 A | 12/2000 | Hinsch et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,180,848 B1 | 1/2001 | Flament et al. | |
| 6,197,935 B1 | 3/2001 | Doillon et al. | |
| 6,201,439 B1 | 3/2001 | Ishida et al. | |
| 6,214,020 B1 | 4/2001 | Mulhauser et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,264,702 B1 | 7/2001 | Ory et al. | |
| 6,267,772 B1 | 7/2001 | Mulhauser et al. | |
| 6,270,530 B1 | 8/2001 | Eldridge et al. | |
| 6,270,792 B1 | 8/2001 | Guillemet et al. | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,306,079 B1 | 10/2001 | Trabucco | |
| 6,319,264 B1 | 11/2001 | Tormala et al. | |
| 6,383,201 B1 | 5/2002 | Dong | |
| 6,425,924 B1 | 7/2002 | Rousseau | |
| 6,447,551 B1 | 9/2002 | Goldmann | |
| 6,485,503 B2 | 11/2002 | Jacobs et al. | |
| 6,500,777 B1 | 12/2002 | Wiseman et al. | |
| 6,596,002 B2 | 7/2003 | Therin et al. | |
| 6,610,006 B1 | 8/2003 | Amid et al. | |
| 6,616,685 B2 | 9/2003 | Rousseau | |
| 6,645,226 B1 | 11/2003 | Jacobs et al. | |
| 6,652,595 B1 | 11/2003 | Nicolo | |
| 6,669,735 B1 | 12/2003 | Pelissier | |
| 6,712,859 B2 | 3/2004 | Rousseau et al. | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,746,458 B1 | 6/2004 | Cloud | |
| 6,755,868 B2 | 6/2004 | Rousseau | |
| 6,790,213 B2 | 9/2004 | Cherok et al. | |
| 6,800,082 B2 | 10/2004 | Rousseau | |
| 6,872,227 B2 | 3/2005 | Sump et al. | |
| 6,926,723 B1 | 8/2005 | Mulhauser et al. | |
| 7,011,688 B2 | 3/2006 | Gryska et al. | |
| 7,021,086 B2 | 4/2006 | Ory et al. | |
| 7,022,358 B2 | 4/2006 | Eckmayer et al. | |
| 7,041,868 B2 | 5/2006 | Greene et al. | |
| 7,060,103 B2 | 6/2006 | Carr, Jr. et al. | |
| 7,070,558 B2 | 7/2006 | Gellman et al. | |
| 7,087,065 B2 | 8/2006 | Ulmsten et al. | |
| 7,094,261 B2 | 8/2006 | Zotti et al. | |
| 7,101,381 B2 | 9/2006 | Ford et al. | |
| 7,156,804 B2 | 1/2007 | Nicolo | |
| 7,156,858 B2 | 1/2007 | Schuldt-Hempe et al. | |
| 7,252,837 B2 | 8/2007 | Guo et al. | |
| 7,279,177 B2 | 10/2007 | Looney et al. | |
| 7,291,294 B2 | 11/2007 | Stolpe et al. | |
| 7,331,199 B2 | 2/2008 | Ory et al. | |
| 7,393,319 B2 | 7/2008 | Merade et al. | |
| 7,404,199 B2 | 7/2008 | Arneson et al. | |
| 7,556,598 B2 | 7/2009 | Rao | |
| 7,594,921 B2 | 9/2009 | Browning | |
| 7,614,258 B2 | 11/2009 | Cherok et al. | |
| 7,732,354 B2 | 6/2010 | Fricke et al. | |
| 7,785,334 B2 | 8/2010 | Ford et al. | |
| 7,789,888 B2 | 9/2010 | Bartee et al. | |
| 7,806,905 B2 | 10/2010 | Ford et al. | |
| 7,824,420 B2 | 11/2010 | Eldridge et al. | |
| 7,828,854 B2 | 11/2010 | Rousseau et al. | |
| 7,869,861 B2 | 1/2011 | Moctezuma de la Barrera et al. | |
| 7,900,484 B2 | 3/2011 | Cherok et al. | |
| 8,100,924 B2 | 1/2012 | Browning | |
| 8,123,817 B2 | 2/2012 | Intoccia et al. | |
| 8,157,821 B2 | 4/2012 | Browning | |
| 8,157,822 B2 | 4/2012 | Browning | |
| 8,182,545 B2 | 5/2012 | Cherok et al. | |
| 8,206,632 B2 | 6/2012 | Rousseau et al. | |
| 8,215,310 B2 | 7/2012 | Browning | |
| 8,562,633 B2 | 10/2013 | Cully et al. | |
| 8,682,052 B2 | 3/2014 | Fitz et al. | |
| 8,758,800 B2 | 6/2014 | Stopek et al. | |
| 2002/0087174 A1 | 7/2002 | Capello | |
| 2002/0099344 A1 | 7/2002 | Hessel et al. | |
| 2002/0131988 A1 | 9/2002 | Foster et al. | |
| 2002/0165601 A1 | 11/2002 | Clerc | |
| 2003/0130745 A1 | 7/2003 | Cherok et al. | |
| 2004/0098118 A1 | 5/2004 | Granada et al. | |
| 2004/0215219 A1 | 10/2004 | Eldridge et al. | |
| 2004/0224007 A1 | 11/2004 | Zhang | |
| 2005/0113849 A1 | 5/2005 | Popadiuk et al. | |
| 2005/0240261 A1 | 10/2005 | Rakos et al. | |
| 2005/0244455 A1 | 11/2005 | Greenawalt | |
| 2005/0261782 A1 | 11/2005 | Hoganson | |
| 2006/0025785 A1 | 2/2006 | Cully et al. | |
| 2006/0034887 A1 | 2/2006 | Pelissier | |
| 2006/0116696 A1 | 6/2006 | Odermatt et al. | |
| 2006/0121078 A1 | 6/2006 | Trogolo et al. | |
| 2006/0188546 A1 | 8/2006 | Giroux | |
| 2006/0224038 A1 | 10/2006 | Rao | |
| 2006/0253203 A1 | 11/2006 | Alvarado | |
| 2006/0282103 A1 | 12/2006 | Fricke et al. | |
| 2007/0088391 A1 | 4/2007 | McAlexander et al. | |
| 2007/0129736 A1 | 6/2007 | Solecki | |
| 2007/0198040 A1 | 8/2007 | Buevich et al. | |
| 2007/0244548 A1 | 10/2007 | Myers et al. | |
| 2007/0260268 A1 | 11/2007 | Bartee et al. | |
| 2007/0299538 A1 | 12/2007 | Roeber | |
| 2008/0017200 A1 | 1/2008 | Carepa et al. | |
| 2008/0109017 A1 | 5/2008 | Herweck et al. | |
| 2008/0113001 A1 | 5/2008 | Herweck et al. | |
| 2008/0118550 A1 | 5/2008 | Martakos et al. | |
| 2008/0161837 A1 | 7/2008 | Toso et al. | |
| 2008/0172071 A1 | 7/2008 | Barker | |
| 2008/0199506 A1 | 8/2008 | Horres et al. | |
| 2008/0255593 A1 | 10/2008 | St-Germain | |

(56) References Cited

U.S. PATENT DOCUMENTS

| | | |
|---|---|---|
| 2009/0036995 A1 | 2/2009 | Lozier et al. |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |
| 2009/0198260 A1 | 8/2009 | Ford et al. |
| 2009/0216338 A1 | 8/2009 | Gingras et al. |
| 2009/0240103 A1* | 9/2009 | Norris .................. D04B 21/12 600/37 |
| 2009/0270999 A1 | 10/2009 | Brown |
| 2009/0276057 A1 | 11/2009 | Trabucco et al. |
| 2009/0281558 A1 | 11/2009 | Li |
| 2009/0299538 A1 | 12/2009 | Suzuki |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0094404 A1 | 4/2010 | Greenhalgh et al. |
| 2010/0104608 A1 | 4/2010 | Abuzaina et al. |
| 2010/0160375 A1 | 6/2010 | King |
| 2010/0286716 A1 | 11/2010 | Ford et al. |
| 2010/0312043 A1 | 12/2010 | Goddard |
| 2010/0318108 A1 | 12/2010 | Datta et al. |
| 2011/0082330 A1 | 4/2011 | Deitch |
| 2011/0144667 A1 | 6/2011 | Horton et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0264120 A1 | 10/2011 | Bayon et al. |
| 2011/0265283 A1 | 11/2011 | Duncan |
| 2011/0293688 A1 | 12/2011 | Bennett et al. |
| 2011/0320009 A1 | 12/2011 | Ladet et al. |
| 2012/0010637 A1 | 1/2012 | Stopek et al. |
| 2012/0016388 A1 | 1/2012 | Houard et al. |
| 2012/0029537 A1 | 2/2012 | Mortarino |
| 2012/0029540 A1 | 2/2012 | Adams |
| 2012/0053602 A1 | 3/2012 | Adzich et al. |
| 2012/0065727 A1 | 3/2012 | Reneker et al. |
| 2012/0082712 A1 | 4/2012 | Stopek et al. |
| 2012/0109165 A1 | 5/2012 | Mathisen et al. |
| 2012/0116423 A1 | 5/2012 | Gleiman et al. |
| 2012/0116425 A1 | 5/2012 | Intoccia et al. |
| 2012/0150204 A1 | 6/2012 | Mortarino et al. |
| 2012/0179175 A1 | 7/2012 | Hammell |
| 2012/0179176 A1 | 7/2012 | Wilson et al. |
| 2012/0239063 A1 | 9/2012 | Lee |
| 2012/0259348 A1 | 10/2012 | Paul |
| 2013/0060263 A1 | 3/2013 | Bailly et al. |
| 2013/0172915 A1* | 7/2013 | Thomas ................ A61F 2/0063 606/151 |

FOREIGN PATENT DOCUMENTS

| | | |
|---|---|---|
| EP | 1674048 A1 | 6/2006 |
| EP | 2016956 A2 | 1/2009 |
| EP | 2314254 A2 | 4/2011 |
| EP | 2353545 A1 | 8/2011 |
| EP | 2404571 A1 | 1/2012 |
| FR | 2601371 A1 | 1/1988 |
| FR | 2857851 A1 | 1/2005 |
| FR | 2924330 A1 | 6/2009 |
| FR | 2949687 A1 | 3/2011 |
| FR | 2949688 A1 | 3/2011 |
| FR | 2951069 A1 | 4/2011 |
| FR | 2953709 A1 | 6/2011 |
| WO | 9311805 A1 | 6/1993 |
| WO | 9806355 A1 | 2/1998 |
| WO | 9951163 A1 | 10/1999 |
| WO | 0180788 A2 | 11/2001 |
| WO | 0181667 A1 | 11/2001 |
| WO | WO01/81667 A1 | 11/2001 |
| WO | 0217853 A2 | 3/2002 |
| WO | 0234304 A1 | 5/2002 |
| WO | 03007847 A1 | 1/2003 |
| WO | 2005028581 A1 | 3/2005 |
| WO | 2006020922 A2 | 2/2006 |
| WO | 2006036967 A1 | 4/2006 |
| WO | 2006040760 A2 | 4/2006 |
| WO | 2006102374 A2 | 9/2006 |
| WO | 2007025266 A2 | 3/2007 |
| WO | 2008127411 A1 | 10/2008 |
| WO | 2009031035 A2 | 3/2009 |
| WO | 2009075786 A1 | 6/2009 |
| WO | 2010043978 A2 | 4/2010 |
| WO | 2010043979 A2 | 4/2010 |
| WO | 2010093333 A1 | 8/2010 |
| WO | 2010129641 A1 | 11/2010 |
| WO | 2011038740 A1 | 4/2011 |
| WO | 2011117758 A2 | 9/2011 |
| WO | 2013098343 A1 | 7/2013 |

* cited by examiner

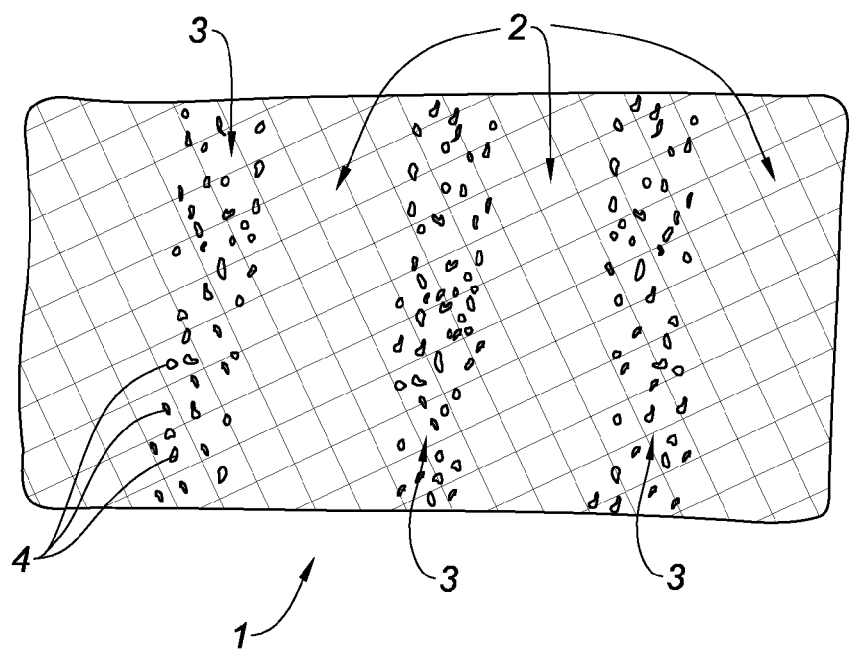

METHOD OF MAKING A KNIT WITH BARBS

CROSS-REFERENCE TO RELATED APPLICATIONS

This application is a National Stage Application of PCT/EP13/063474 under 35 USC §371 (a), which claims priority of French Patent Application Serial No. 12/56168 filed Jun. 28, 2012, the disclosures of each of the above-identified applications are hereby incorporated by reference in their entirety.

The present invention relates to a method for producing a prosthetic knit made in one piece, of which at least one face has one or more zones provided with barbs, and one or more zones free of barbs. Such a knit can be used in particular for producing prostheses that require variable fastening capabilities, for example for fastening to biological tissues, on the surface of said prosthesis.

Wall reinforcement prostheses, for example for the abdominal wall, are widely used in surgery. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to be fitted. Some of these prostheses are made from entirely bioresorbable yarns and are intended to disappear after having performed their reinforcing role while cell colonization takes place and tissue rehabilitation takes over. Others comprise non-bioresorbable yarns and are intended to remain permanently in the body of the patient.

Some of these prostheses are made from an arrangement of yarns, a knit, a woven or non-woven fabric, comprising barbs protruding outwards from one face of the prosthesis: these barbs constitute hooks that are able to fix themselves either in another prosthetic fabric, belonging to the same prosthesis or not, or directly in the biological tissues, for example the abdominal wall.

The presence of barbs capable of fastening themselves directly to biological tissues makes it possible to do away with additional means of attachment for the prosthesis, such as staples, sutures, etc. However, in certain cases, for example when the prosthesis is to be implanted in the vicinity of weak or sensitive organs, such as vessels, nerves, or else the spermatic cord, it may prove advantageous for the part of the prosthesis in contact with these organs to be free of such barbs.

In such cases, a composite prosthesis is generally produced comprising a first textile portion with barbs and a second textile portion without barbs that is assembled to the first portion, for example by means of stitching, or ultrasonic welding, etc. Such a process is tedious and complicated. Furthermore, due to the discontinuous nature of the textile making up the composite prosthesis thus obtained, the mechanical properties of the prosthesis are not the same over the whole of the prosthesis. In particular, the area where the first textile portion is joined to the second textile portion may constitute a line of weakness of the prosthesis.

Alternatively, a textile comprising barbs protruding outwards from one of its faces across one or more specific zones can be produced by manually incorporating barbs or hooks into said textile on said one or more specific zones after knitting. However, such work is lengthy and tedious.

There therefore remains a need for a method for simple and rapid production of a knit that would provide a reinforcing prosthesis with zones that have good fastening capabilities and also with smoother and non-traumatizing zones.

The present invention aims to meet this need by proposing a simple and rapid method for producing a knit made in one piece, of which at least one face has one or more zones provided with barbs and one or more zones free of such barbs.

The present invention relates to a method for producing a prosthetic knit made in one piece, said method comprising the following steps:

a) knitting, on at least three guide bars of a warp knitting machine or raschel knitting machine, first yarns of biocompatible polymer materials, a second yarn, which is a monofilament yarn, and a third yarn, which is a monofilament yarn, said second yarn and third yarn being made of the same biocompatible hot-melt material, the second yarn having a diameter D2, the third yarn having a diameter D3, such that D3 is strictly smaller than D2, according to the following distribution:

a first guide bar B1 and a second guide bar B2 are threaded continuously with said first yarns over the entire width of said knitting machine and form mutually opposite first and second faces for said knit, a third guide bar B3 is threaded intermittently with said second yarn and third yarn, the chart followed by said second and third yarns generating loops protruding outwards from at least the first face of said knit, b) thermosetting the knit obtained at a), c) placing the first face of the knit, provided with said loops, flat on a cylinder brought to a temperature T resulting in i) the complete melting of the loops formed from said third yarn and the elimination of every part of these loops protruding outwards from the first face of said knit, and ii) the partial melting of the loops formed from said second yarn, said partial melting causing the rupture of each loop and, therefore, the formation, from each loop, of two barbs protruding outwards from the first face of said knit.

Thus, according to the method of the invention, only some of the loops generated by the second and third yarns of bar B3 will give rise to barbs. In particular, since the second and third yarns are made of the same hot-melt material but each have different diameters, these yarns will not react in the same way upon contact with the cylinder heated to the temperature T during step c). Indeed, since the third yarn has a diameter strictly smaller than the diameter of the second yarn, it will melt much more quickly than the second yarn when these second and third yarns are exposed to the same temperature.

In the method according to the invention, the temperature T is chosen such that it causes the complete melting of the loops formed by the third yarn, and the partial melting of the loops formed by the second yarn, when the cylinder presses flat against the face of the knit, provided with the loops, for a defined period of time. The temperature T is determined depending on the nature of the hot-melt material forming the second and third yarns.

Thus, during step c) of the method according to the invention, the loops formed from the third yarn melt completely, and the part of the loop initially protruding outwards from the face of the knit is consequently eliminated: at the end of step c), no part of the loops originating from the third yarn is left protruding outwards from the face of the knit.

By contrast, during step c), the loops formed from the second yarn melt only partially, in the area of their summit in contact with the cylinder. The loop is thus cut in two, as is described in WO01/81667. This break generates two barbs, each of them having a head with dimensions greater than its stem, this stem having the diameter D2 of the second yarn.

Thus, at the end of step c), the only zones of the knit that have barbs protruding outwards from the face of the knit are the ones where the loops were formed from the second yarn.

The method according to the invention makes it possible to obtain a knit having barbs only on one or more defined zones of one face for example, and to do this in a single knitting step, without the need for a supplementary step. Thus, the method according to the invention is simple and quick and does not require a step in which barbs are fastened manually to a specific zone of a face after knitting.

The method according to the invention permits industrial-scale production of a knit that has barbs on chosen areas. Such a knit can thus be fastened to biological tissues by one or more of said specific zones provided with barbs, whereas the rest of the knit, free of barbs, can be placed opposite weaker anatomical zones. In a further alternative, the knit obtained by the method according to the invention can be fastened, by means of its one or more specific zones provided with barbs, to another textile: it may thus be used to assemble two textiles without the need for staples.

Moreover, the partial melting of the loops formed from a monofilament makes it possible to obtain barbs that have a head with dimensions greater than the diameter of the monofilament, said head thus being well suited to its functions of fastening and fixing, either to biological tissues or to other textiles, in particular openwork textiles. Within the meaning of the present invention, openwork textile means the characteristic whereby a textile has pores, or voids, cells, holes or orifices that are open and distributed uniformly or non-uniformly and that promote cellular colonization. The pores can be present in all sorts of forms, for example spheres, channels and hexagonal shapes.

In the present application, a "prosthetic knit" is understood as a knit intended to be implanted in the human or animal body in the form of a prosthesis or any other part designed at least in part with said knit.

According to the present application, a knit made in one piece means that the knit is produced in a single knitting step and does not comprise additional textile added by any means of attachment, such as stitching, ultrasonic welding, etc. Thus, the knit according to the invention has mechanical properties that are constant over the whole of its surface, whether on the zones comprising barbs or on the zones free of barbs.

In a first step of the method according to the invention, a knit is produced, on at least three guide bars of a warp knitting machine or raschel knitting machine, from first yarns of biocompatible polymer materials, from a second yarn, which is a monofilament yarn, and from a third yarn, which is a monofilament yarn, said second yarn and third yarn being made of the same biocompatible hot-melt material, the second yarn having a diameter D2, the third yarn having a diameter D3, such that D3 is strictly smaller than D2.

The first yarns of the knit according to the invention can be monofilament and/or multifilament yarns, and they can be made from any biodegradable or non-biodegradable biocompatible material. Thus, the biodegradable materials suitable for the first yarns of the knit of the present invention can be chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, copolymers thereof, and mixtures thereof. The non-biodegradable materials suitable for the first yarns of the knit of the present invention can be chosen from among polyethylene terephthalate (PET), polyamides, aramids, expanded polytetrafluoroethylene, polyurethane, polyvinylidene difluoride (PVDF), polybutyl esters, PEEK (polyether ether ketone), polyolefins (such as polyethylene or polypropylene), copper alloys, silver alloys, platinum, medical grades of steel such as medical-grade stainless steel, and combinations thereof.

When the first yarns are monofilaments, they can have any diameter that allows a base knit to be obtained which is suitable for the production of a prosthesis for a hernia. For example, the diameter of the first yarns, when they are monofilaments, can vary from 80 μm to 200 μm.

In the method according to the invention, at least a first guide bar B1 and a second guide bar B2 are threaded continuously with said first yarns over the entire width of said knitting machine and form mutually opposite first and second faces for said knit. The formation of a base knit of this kind is well known and will not be explained in any more detail here. For example, the base knit could be produced from a number of guide bars greater than two, for example three or four guide bars. By way of example, said first yarns can be threaded on the two guide bars B1 and B2, according to the following chart in accordance with ISO 11676:

bar B1: 1.0/0.1//
bar B2: 1.0/5.5/1.0/3.3//

An openwork knit is thus obtained having a first face and an opposite second face. The bars B1 and B2 permit production of the base knit, which gives the knit its cohesion and stability.

The second yarn and the third yarn are monofilament yarns made from the same biocompatible hot-melt material. This hot-melt material can be biodegradable or non-biodegradable and can be chosen from among all the materials cited above for the first yarns, these materials being hot-melt materials. Thus, the hot-melt material forming said second and third yarns can be chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, polyethylene terephthalate (PET), aramids, expanded polytetrafluoroethylene, polyurethane, polyvinylidene difluoride (PVDF), polybutyl esters, PEEK (polyether ether ketone), polyolefins (such as polyethylene or polypropylene), copper alloys, silver alloys, platinum, medical grades of steel such as medical-grade stainless steel, copolymers thereof, and mixtures thereof.

In one embodiment, the hot-melt material is bioresorbable. It is thus possible to produce prostheses having temporary fastening zones: in other words, once the prosthesis has been colonized by cells after implantation, the barbs, of which the fastening function is no longer needed, resorb naturally.

Thus, in one embodiment, the hot-melt material forming said second and third yarns can be chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, copolymers thereof, and mixtures thereof.

For example, the hot-melt material forming said second and third yarns is polylactic acid.

According to the method of the invention, the second yarn has a diameter D2, and the third yarn has a diameter D3, such that D3 is strictly smaller than D2.

Thus, as was seen above, during the step in which the face of the knit provided with the loops is pressed flat against the cylinder heated to the temperature T, the loops formed from the second yarn will not react in the same way as the loops formed from the third yarn. In particular, the loops formed from the second yarn will be simply cut in two and will generate barbs, whereas the loops formed from the third yarn will be completely melted and their initially protruding part will be eliminated.

In one embodiment, D2≥130 μm, and 70 μm≤D3<130 μm. Such ranges of the respective diameters for the second yarn and the third yarn effectively permit the complete melting of the loops originating from the third yarn and the partial melting of the loops originating from the second yarn, during step c).

In the method according to the invention, the second and third yarns are the yarns that will generate the loops. These yarns are threaded on a single guide bar, namely bar B3.

Charts resulting in the formation of loops are known and, for example, are described in WO01/81667. By way of example, the bar B3, forming the loops, follows the chart below in accordance with ISO 11676:

B3: 2-1/5-5/3-4/0-0//

For example, the loops protrude outwards from the first face by a length of 1 to 2 mm, preferably by a length of approximately 1.5 mm. Such a height of the loops makes it possible in particular to preserve the integrity of the first yarns forming the base knit when pressing the knit flat against the heated cylinder in step c).

The second yarn and the third yarn in the method according to the invention are different, their respective diameters being different. However, since these yarns are threaded on a single guide bar, namely bar B3, they are therefore threaded intermittently on this bar B3: in other words, each yarn is not threaded continuously over the width of the knitting machine, and instead the two yarns are threaded in alternation, which alternation may be regular or non-regular according to the threading plan determined in advance, depending on the number of zones with barbs that are to be obtained and depending on the desired shape for said one or more zones with barbs. The second yarn and the third yarn are thus arranged depending on the desired result.

For example, in one embodiment, the plan for intermittent threading of bar B3 is:

$$N \times [m_2 \times (1 \text{ full } F2-1 \text{ empty}), m_3 \times (1 \text{ full } F3-1 \text{ empty})]$$

where $m_2$ is from 1 to 100, $m_3$ is from 1 to 100, F2 is the second yarn, F3 is the third yarn, and N is the number of times the threading has to be repeated in order to attain the width of the desired knit, for example the width of the knitting machine. The threading of the second and third yarns over the entire width of the knitting machine makes it possible to generate loops over the whole surface of the face of the knit and protects the first yarns, forming the base knit, by keeping the heated cylinder at a distance from these first yarns in step c) of the method according to the invention.

For example, $m_2=2$, and $m_3=4$. In another embodiment, $m_2=4$, and $m_3=2$. In another embodiment, $m_2=3$, and $m_3=3$. In another embodiment, $m_2=30$, and $m_3=15$.

As will be described below, during step c) of the method according to the invention, the loops formed from F3 will be completely melted and will no longer have any part left protruding from the face of the knit. Thus, the zones of the knit corresponding to the N threaded portions $m_3\times(1 \text{ full } F3-1 \text{ empty})$ will be free of barbs, whereas the zones of the knit corresponding to the N threading portions $m_2\times(1 \text{ full } F2-1 \text{ empty})$ will be provided with barbs: thus, in the present example, the zones free of barbs and the zones provided with barbs will have the shape of longitudinal bands.

In a second step of the method according to the invention, the knit obtained at step a) is thermoset. This thermosetting is done in a conventional manner.

In a third step of the method according to the invention, the first face of the knit, provided with said loops, is pressed flat on a cylinder brought to a temperature T resulting in i) the complete melting of the loops formed from said third yarn and the elimination of every protruding part of these loops, and ii) the partial melting of the loops formed from said second yarn, said partial melting causing the rupture of each loop and, therefore, the formation, from each loop, of two barbs protruding outwards from the first face of said knit.

A device for carrying out step c), such as the cylinder to press flat on the face of the knit comprising the loops, is described in the document WO01/81667, for example. Generally, the knit is guided between several unheated rollers in order to confer upon it a movement, at a constant speed, in the direction of a cylinder heated to a temperature T, such that the face of the knit provided with the loops comes into contact with this cylinder.

As has been explained above, in the method according to the invention the temperature T is chosen such that it causes the complete melting of the loops formed from the third yarn, and the partial melting of the loops formed from the second yarn, when the cylinder is pressed flat against the face of the knit provided with the loops during the constant movement of the knit with respect to the cylinder.

Thus, in one embodiment, the temperature T is higher than or equal to the melting temperature of the hot-melt material. Preferably, the temperature T is strictly higher than the melting temperature of the hot-melt material.

Thus, during the step c) of the method according to the invention, the loops formed from the third yarn melt completely and the part of the loop initially protruding outwards from the face of the knit is consequently eliminated: at the end of step c), no part of the loops originating from the third yarn is left protruding outwards from the face of the knit.

By contrast, during this step c), the loops formed from the second yarn melt only partially, in the area of their summit in contact with the cylinder. The loop is thus cut in two, as is described in WO01/81667. This break generates two barbs, each of them having a head with dimensions greater than its stem, this stem having the diameter D2 of the second yarn.

Thus, at the end of step c), the only zones of the knit that have barbs protruding outwards from the face of the knit are the ones where the loops were formed from the second yarn.

In one embodiment of the method according to the invention, the hot-melt material is polylactic acid, D2=150 μm and D3=80 μm, and the temperature T of step c) is 225° C. The melting temperature of the polylactic acid is 185-195° C.

In the one or more zones where they are present, the barbs of the knit thus obtained can protrude from the first face substantially perpendicularly with respect to the plane of said face or, alternatively, in one or more planes inclined with respect to said face.

For example, the first face of the knit obtained by the method according to the invention can comprise several zones free of barbs, these zones being intended to be situated opposite weak or sensitive organs once the prosthesis or the knit has been implanted, while the rest of the first face of the knit is provided with barbs situated opposite other organs, for example muscles, in which they will be able to fasten themselves in order to fix the knit or the prosthesis in place.

Alternatively, these barbs may be intended to be entangled in one or more arrangements of yarns, fibres, filaments and/or multifilaments of another prosthetic textile, for example in order to form a composite reinforcing prosthesis, in particular if it is desired, for example, that only certain zones of the knit obtained according to the invention fasten themselves in this other prosthetic textile.

Thus, it is possible to prepare knits having a central longitudinal zone free of barbs, and two lateral longitudinal zones provided with barbs. For example, it is possible to cut out transversely, from such a knit, prostheses for the production of bands for treating urinary incontinence in women, such bands having a relatively smooth and atraumatic central portion for placing opposite the urethra, and corresponding to the central longitudinal zone of the knit during the production thereof before cutting, and two outermost portions with barbs for fixing in the surrounding tissues, these two outermost portions of the prosthesis corresponding to the two lateral longitudinal zones of the knit during the production thereof before cutting.

In one embodiment, said barbs protrude outwards from the first face by a length of 1 to 2 mm, preferably by a length of approximately 1.5 mm.

Such a length of the barbs permits good fastening of the barbs in the biological tissues and also an optimized method of production.

The advantages of the present invention will become clear from the following example and from the attached drawing, in which:

FIG. 1 is a plan view of a prosthetic knit obtained by the method of the invention.

Referring to FIG. 1, a knit 1 is shown that is obtained by cutting out a rectangle from a prosthetic knit obtained by the method according to the invention. The knit 1 comprises zones 2 free of barbs, and zones 3 comprising barbs 4 protruding outwards from the upper face of the knit 1. The zones 2 free of barbs correspond to the portions threaded with the second yarn (F2) of the method according to the invention, while the zones 3 provided with barbs correspond to the portions threaded with the third yarn (F3) of the method according to the invention. In the present example, the zones 2 free of barbs and the zones 3 provided with barbs are shaped as bands.

Said barbs 4 generally protrude outwards from the face of the knit 1 by a length of 1 to 2 mm, preferably by a length of approximately 1.5 mm. Such a length of the barbs permits good fastening of the barbs in the biological tissues and also an optimized method of production.

The zones 2 free of barbs may be intended, for example, to be situated opposite weak or sensitive organs once the knit 1 has been implanted, while the zones 3 provided with barbs can be situated opposite other organs, for example muscles, in which they will be able to fasten themselves in order to fix the knit 1 in place.

Alternatively, the barbs 4 may be intended to be entangled in one or more arrangements of yarns, fibres, filaments and/or multifilaments of another prosthetic textile, for example in order to form a composite reinforcing prosthesis, particularly if it is desired, for example, that only certain zones of the knit 1 should fasten themselves in this other prosthetic textile.

The method according to the invention permits industrial-scale production of a knit that has barbs on chosen areas. Such a knit can thus be fastened to biological tissues by one or more of said specific zones provided with barbs, while the rest of the knit, free of barbs, can be placed opposite weaker anatomical zones. In a further alternative, the knit obtained by the method according to the invention can be fastened, by means of its one or more specific zones provided with barbs, to another textile: it may thus be used to assemble two textiles without the need for staples.

EXAMPLE 1

A knit having zones free of barbs and zones provided with barbs is produced by the method according to the invention as described below.

A knit is produced on a warp knitting machine, by means of three guide bars B1, B2 and B3, using the following chart in accordance with ISO 11676:
bar B1: 1.0/10.1//
bar B2: 1.0/5.5/1.0/3.3//
bar B3: 2.1/5.513.4/0.0//

Bar B1 and bar B2 are each threaded continuously 1 full, 1 empty, over the width of the knitting machine with a monofilament yarn of polylactic acid having a diameter of 80 μm.

Bar B3, which will give rise to the loops, is threaded intermittently with two hot-melt monofilament yarns of polylactic acid: a yarn called F2, corresponding to the second yarn of the above description and having a diameter D2=150 μm, and a yarn called F3, corresponding to the third yarn of the above description and having a diameter D3=80 μm, in accordance with the following threading plan:

$$N \times [4 \times (1 \text{ full } F2-1 \text{ empty}), 2 \times (1 \text{ full } F3-1 \text{ empty})]$$

where N is the number of times the threading has to be repeated in order to attain the width of the knitting machine.

The melting temperature of the polylactic acid used for yarns F2 and F3 is 185-195° C.

The knitting in accordance with the above chart results in the formation of loops protruding outwards from one face of the knit, some of these loops being formed by the yarn F2, the other loops being formed by the yarn F3. Since the bar B3 is threaded over the width of the knitting machine, loops are present over the whole surface of one face of the knit. The loops protrude outwards from one face of the knit by a length of 1 to 2 mm, preferably by a length of approximately 1.5 mm.

The knit thus obtained is thermoset in a conventional manner.

The face of the knit provided with the loops is then placed flat on a cylinder heated to a temperature of 225° C. A device for carrying out this step is described in the document WO01/81667, for example. The knit is guided between several unheated rollers in order to confer upon it a movement, at a constant speed, in the direction of the cylinder heated to 225° C., against which it is placed flat such that the loops come into contact with this cylinder. However, during this placement, the yarns of bars B1 and B2 forming the base knit are kept at a distance from the heated cylinder on account of the presence, over the entire width of the knitting machine, of the loops having a height of approximately 1 to 2 mm. Thus, the base knit (excluding loop) is not brought into contact with the heated cylinder and maintains its integrity.

When the knit is thus placed flat, the loops originating from the yarn F3 completely melt, and the parts of these loops initially protruding outwards from the face of the knit are consequently eliminated and/or crushed into the body of the knit.

By contrast, still during this placing flat, the loops originating from the yarn F2 melt only partially, in the area of their summit in contact with the cylinder. Each loop is thus cut in two, as is described in WO01/81667. This break thus generates two barbs per loop. These barbs, for example, have the shape of a stem, with the diameter of the yarn F2, i.e. 150 μm, surmounted by a head with a diameter greater than that of the stern. The barbs protrude outwards from the face of the knit by a length of approximately 1.5 mm. Such a length of the barbs permits good fastening of the barbs in the biological tissues upon implantation of the knit or of a prosthesis comprising this knit.

In the knit obtained at the end of this step of placing it flat against the cylinder heated to 225° C., the zones of the knit corresponding to the N threaded portions 2×(1 full F3–1 empty) are free of barbs, whereas the zones of the knit corresponding to the N threading portions 4×(1 full F2–1 empty) are provided with barbs: the knit in the present example therefore has a succession of longitudinal bands free of barbs and longitudinal bands provided with barbs.

The knit in this example can be used just as it is, or in combination with other textiles in order to form reinforcing prostheses that have zones with good fastening capabilities and also zones that are smoother and do not cause trauma.

By varying the threading plan of bar B3 with yarns F2 and F3, it is possible to modify the number of zones with or without barbs, and also the shape of these zones, with a view to adapting these zones to the constraints (weak organs, etc.) of the anatomical region treated with prostheses that comprise such knits.

The invention claimed is:

1. Method for producing a prosthetic knit made in one piece, said method comprising:
   a) knitting, on at least three guide bars of a warp knitting machine or raschel knitting machine, first yarns of biocompatible polymer materials, a second yarn, which is a monofilament yarn, and a third yarn, which is a monofilament yarn, said second yarn and third yarn being made of the same biocompatible hot-melt material, the second yarn having a diameter D2, the third yarn having a diameter D3, such that D3 is strictly smaller than D2, according to the following distribution:
      a first guide bar B1 and a second guide bar B2 are threaded continuously with said first yarns over an entire width of said knitting machine and form mutually opposite first and second faces for a knit,
      a third guide bar B3 is threaded intermittently with said second yarn and third yarn, said second and third yarns generating loops protruding outwards from at least the first face of said knit,
   b) thermosetting the knit obtained at a),
   c) placing the first face of the knit, provided with said loops, flat on a cylinder brought to a temperature T resulting in i) a complete melting of the loops formed from said third yarn and an elimination of every part of the loops protruding outwards from the first face of said knit, and ii) a partial melting of the loops formed from said second yarn, said partial melting causing a rupture of each loop and, therefore, a formation, from each loop, of two barbs protruding outwards from the first face of said knit.

2. The method according to claim 1, wherein the biocompatible hot-melt material forming said second and third yarns is chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, polyethylene terephthalate (PET), aramids, expanded polytetrafluoroethylene, polyurethane, polyvinylidene difluoride (PVDF), polybutyl esters, PEEK (polyether ether ketone), polyolefins, copper alloys, silver alloys, platinum, medical grades of steel, copolymers thereof, and mixtures thereof.

3. The method according to claim 1, wherein said biocompatible hot-melt material is bioresorbable.

4. The method according to claim 1, wherein said biocompatible hot-melt material is chosen from among polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyesters, copolymers thereof, and mixtures thereof.

5. The method according to claim 4, wherein said biocompatible hot-melt material is polylactic acid.

6. The method according to claim 1, wherein
   $D2 \geq 130\mu m$, and
   $70\mu m \leq D3 < 130\mu m$.

7. The method according to claim 1, wherein the temperature T is higher than or equal to, a melting temperature of the biocompatible hot-melt material.

8. The method according to claim 5, wherein $D2 = 150\mu m$ and $D3 = 80\mu m$, and the temperature T in step c) is 225° C.

9. The method according to claim 1 wherein the third guide bar B3 forming the loops follows a chart shown below in accordance with ISO 11676:
   B3: 2-1/5-5/3-4/0-0//.

10. The method according to claim 1 wherein said first yarns are threaded on the first and second guide bars B1 and B2, according to the following chart in accordance with ISO 11676:
    bar B1: 1.0/0.1//
    bar B2: 1.0/5.5/1.0/3.3//.

11. The method according to claim 1 wherein a threading plan for intermittent threading of the third guide bar B3 is:

$N \times [m_2 \times (1 \text{ full } F2-1 \text{ empty}), m_3 \times (1 \text{ full } F3-1 \text{ empty})]$ where $m_2$ is from 1 to 100, $m_3$ is from 1 to 100, F2 is the second yarn, F3 is the third yarn, and N is the number of times a threading has to be repeated in order to attain a desired width of the knit.

12. The method according to claim 11, wherein $m_2 = 2$, and $m_3 = 4$.

13. The method according to claim 11, wherein $m_2 = 4$, and $m_3 = 2$.

14. The method according to claim 11, wherein $m_2 = 3$, and $m_3 = 3$.

15. The method according to claim 11, wherein $m_2 = 30$, and $m_3 = 15$.

* * * * *